United States Patent [19]

Shoesmith

[11] Plant 4,807

[45] Jan. 19, 1982

[54] CHRYSANTHEMUM NAMED HAWKEYE

[75] Inventor: Leonard H. Shoesmith, Westfield-Woking, England

[73] Assignee: Pan-American Plant Company, West Chicago, Ill.

[21] Appl. No.: 170,074

[22] Filed: Jul. 18, 1980

[51] Int. Cl.[3] ..... A01H 5/00

[52] U.S. Cl. ..... Plt./74

[58] Field of Search ..... Plt./70, 74

*Primary Examiner*—Robert E. Bagwill

*Attorney, Agent, or Firm*—Chas. W. Rummler

[57] ABSTRACT

A new chrysanthemum cultivar for fall garden culture having a profuse production of relatively small, daisy-like flowers which form a dense mound of color. This plant has a rapid and vigorous growth habit and blooms naturally in the mid-season of fall, growing to a height of about 50 to 75 centimeters. This plant may also be grown as a year-round four inch pot plant and will not become vegetative and rosette under cool temperatures.

4 Drawing Figures

BACKGROUND OF THE NEW PLANT

This new chrysanthemum cultivar originated as a seedling of unknown parentage and was discovered by me in 1976 growing among a group of chrysanthemum plants maintained at West Chicago, Ill., for breeding purposes. This plant attracted my attention because of its apparent superiority, in both vigor and growth, over the companion variety "Yellow Jacket" (U.S. Plant Pat. No. 4,244). Accordingly, I reproduced the original plant at West Chicago, Ill., by means of cuttings for observation and test purposes and subsequently, under my direction, this plant was propagated by cuttings through successive generations for both garden and four inch pot culture, which showed that its novel characteristics hold true from generation to generation and appear to be firmly fixed. This plant is now being propagated for commercial purposes at West Chicago, Ill., and at Cortez, Fla.

DESCRIPTION OF THE DRAWINGS

This new chrysanthemum cultivar is illustrated by the accompanying drawings, of which sheet one is a full color photographic view showing a garden plant in full bloom; sheet two is a photographic close-up face view of the flowers of the new plant which has been hand-painted to show the true colors of the blooms according to specification; and sheet three is a machine copy of typical leaves of this new variety.

DESCRIPTION OF THE NEW PLANT

The following is a detailed description of my new chrysanthemum cultivar based upon observations of plants grown at West Chicago, Ill., and made in the fall of 1979, the color designations being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Fall garden chrysanthemum.

Form: Herbaceous bush of mound shape.
Height: 50 to 75 cm.

Growth: Vigorous, strong and upright with a rapid growth rate.
Branching character: Caespitose.
Foliage:
- *Quantity.*—Abundant.
- *Size of leaf.*—About 25 to 55 mm. long and about 20 to 40 mm. wide.
- *Leaf shape.*—Ovate with cleft margins.
- *Texture.*—Leathery.
- *Venation.*—Pinnate.
- *Color.*—Upper side — 147A. Under side — 147B.
- *Petioles.*—Length — about 5 to 20 mm.

THE BUD

Form: Globular.
Size: The size varies in both diameter and length.
Opening rate: Normal.
Color of florets: When phyllaries first divide — 7A. When petals begin to unfurl — 7A.
Phyllaries:
- *Number.*—Approximately 15.
- *Shape.*—Lanceolate.
- *Color.*—138B.

Peduncle: Rigid and erect and of variable lengths.
- *Surface aspect.*—Canescent.
- *Color.*—138B.

THE FLOWER

Blooming habit: Intermittent, blooming profusely in the mid-season of fall.
Blooms:
- *Size.*—Small. Diameter — 25 to 35 mm. Depth — 8 to 10 mm.

Borne: Cyme.
Shape:
- *When bloom first opens.*—Cup-shaped.
- *As the bloom matures.*—Flat.

Petalage:
- *Ray florets.*—Approximately 30 in number.
- *Disc florets.*—Many.
- *Arrangement.*—Imbricated.
- *Form.*—Elliptic with entire margins and rounded apex.

Texture: Soft.
Appearance: Satiny.
Color:

*Outer petals.*—Both body and base — 7A. Reverse side — 7B.

*Disc.*—14A at margin fading to 151A at center.

*Pollen.*—14A.

Persistence: The florets hang on and dry.

Peduncle: Strong, upright and of variable lengths.

*Color.*—138B.

Fragrance: Typical chrysanthemum.

Lasting quality: On the plant — four weeks. Not recommended as cut flower.

REPRODUCTIVE ORGANS

Stamens:

*Arrangement.*—Syngenesious.

*Number.*—Many.

*Anthers.*—Size — insignificant. Color — yellow.

*Filaments.*—Length — insignificant. Color — yellow.

*Pollen.*—Color — yellow.

Pistils:

*Number.*—One for each floret.

*Styles.*—Length — insignificant. Color — yellow.

Stigmas:

*Color.*—Yellow.

Ovaries: Inferior and bicarpellate.

This new chrysanthemum cultivar most nearly resembles the variety "Yellow Jacket" (U.S. Plant Pat. No. 4,244). This new plant is superior to "Yellow Jacket", however, in that it is more vigorous in growth and forms a larger mound of bright yellow daisy-like flowers. Like "Yellow Jacket", this new cultivar may be grown as a fall garden chrysanthemum with medium response. Unlike "Yellow Jacket", however, this new variety may be grown as a year-round four inch pot plant and will not become vegetative and rosette under cooler temperatures.

I claim:

1. A fall garden chrysanthemum cultivar, substantially as herein shown and described, characterized in uniqueness, when compared with the variety "Yellow Jacket", by its more vigorous growth which forms a larger mound of bright yellow daisy-like flowers, and by its capability of being grown as a year-round four inch pot plant.

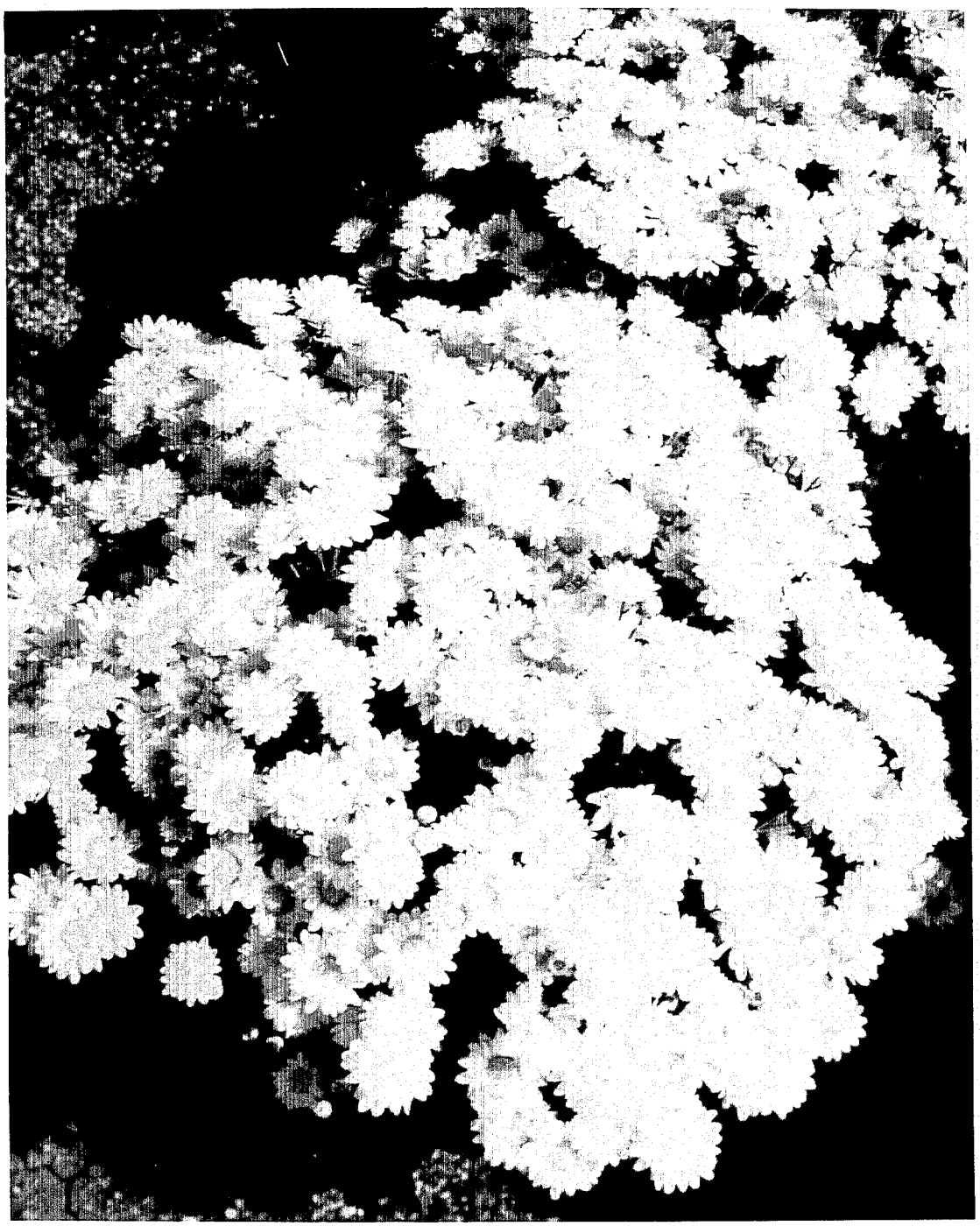

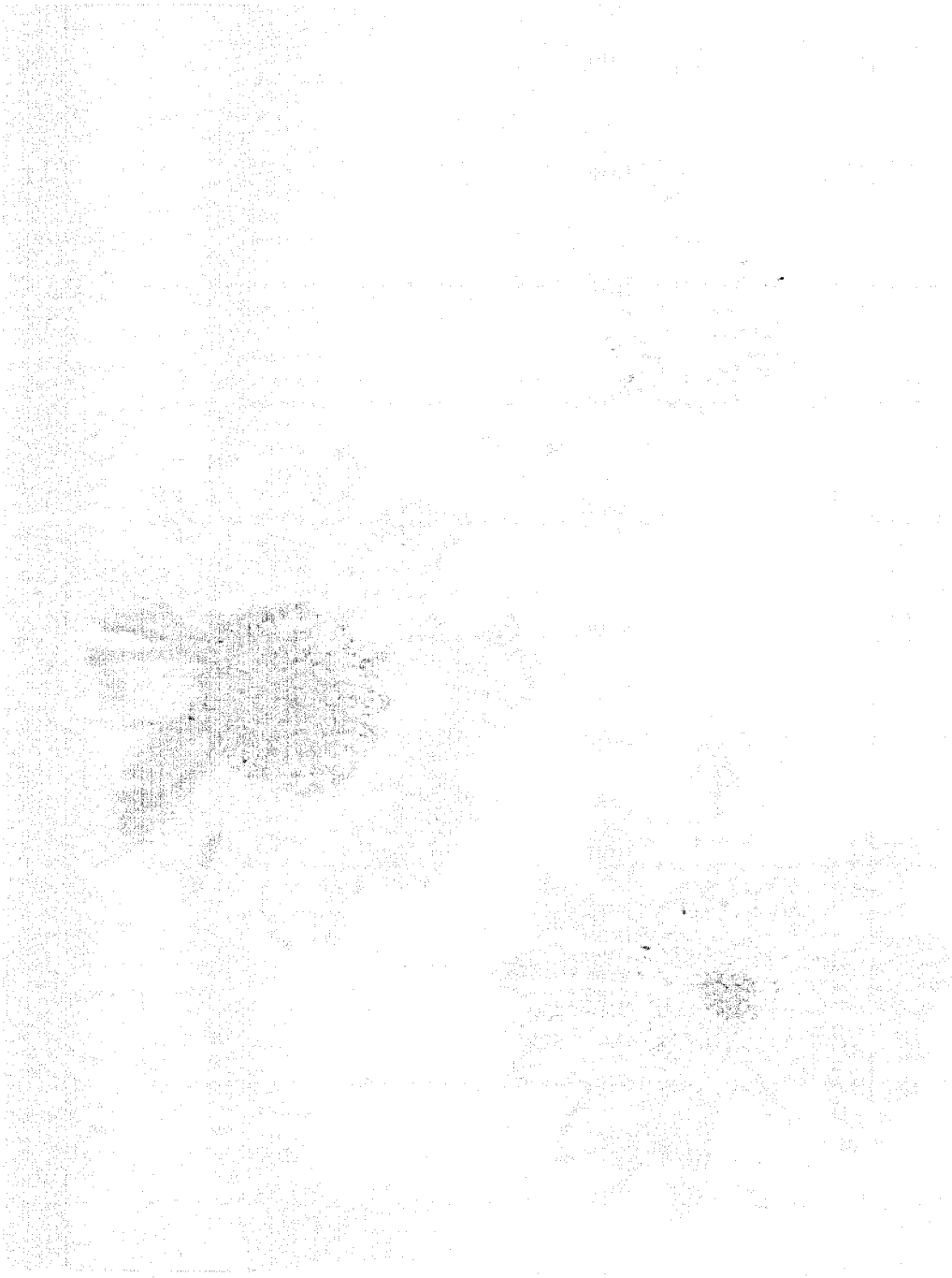

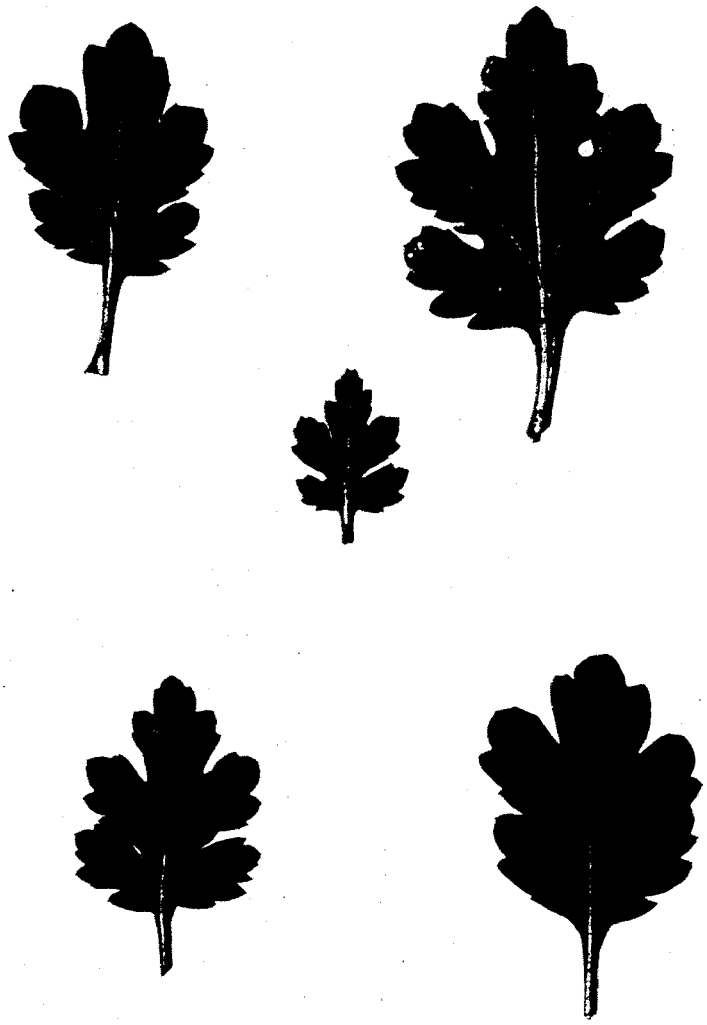

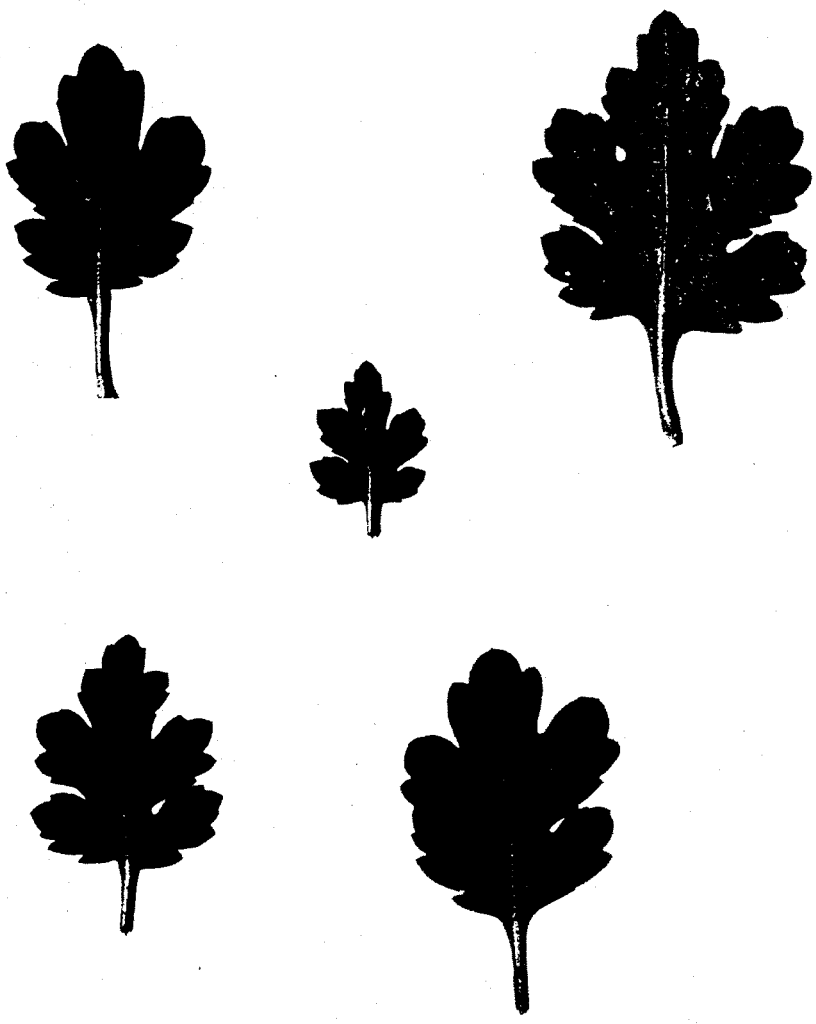

* * * * *